(12) United States Patent
Offenhaeuser et al.

(10) Patent No.: US 9,277,881 B2
(45) Date of Patent: Mar. 8, 2016

(54) METHOD AND DEVICE FOR DETECTING THE CONDITION OF A DRIVER

(71) Applicant: Robert Bosch GmbH, Stuttgart (DE)

(72) Inventors: Andreas Offenhaeuser, Marbach am Neckar (DE); Ernst Schermann, Leinfelden-Echerdingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 14/403,504

(22) PCT Filed: May 22, 2013

(86) PCT No.: PCT/EP2013/060458
§ 371 (c)(1),
(2) Date: Nov. 24, 2014

(87) PCT Pub. No.: WO2013/174838
PCT Pub. Date: Nov. 28, 2013

(65) Prior Publication Data
US 2015/0094907 A1 Apr. 2, 2015

(30) Foreign Application Priority Data
May 25, 2012 (DE) .......... 10 2012 208 822

(51) Int. Cl.
| | | |
|---|---|---|
| A61B 5/00 | (2006.01) |
| A61B 5/18 | (2006.01) |
| G08B 21/06 | (2006.01) |
| A61B 5/0205 | (2006.01) |
| B60W 40/09 | (2012.01) |
| G01J 1/42 | (2006.01) |
| G08B 29/18 | (2006.01) |
| A61B 5/01 | (2006.01) |
| A61B 5/024 | (2006.01) |
| B60W 40/08 | (2012.01) |

(52) U.S. Cl.
CPC .............. *A61B 5/18* (2013.01); *A61B 5/02055* (2013.01); *B60W 40/09* (2013.01); *G01J 1/4204* (2013.01); *G08B 21/06* (2013.01); *A61B 5/01* (2013.01); *A61B 5/024* (2013.01); *B60W 2040/0827* (2013.01); *B60W 2540/18* (2013.01); *G08B 29/18* (2013.01)

(58) Field of Classification Search
CPC .......... G08B 21/06; G08B 23/00; A61B 5/16; A61B 5/18
USPC ............................ 701/34.4, 36; 340/575, 576
See application file for complete search history.

(56) References Cited

U.S. PATENT DOCUMENTS

| | | | | |
|---|---|---|---|---|
| 5,521,580 A | * | 5/1996 | Kaneko et al. ................ 340/439 |
| 5,805,720 A | * | 9/1998 | Suenaga et al. ............... 382/117 |
| 6,049,747 A | * | 4/2000 | Nakajima ............. B60N 2/002 |
| | | | | 340/576 |

(Continued)

FOREIGN PATENT DOCUMENTS

| | | |
|---|---|---|
| CN | 101686816 A | 3/2010 |
| CN | 202183154 U | 4/2012 |

(Continued)

*Primary Examiner* — Thomas Tarcza
*Assistant Examiner* — Tyler J Lee
(74) *Attorney, Agent, or Firm* — Kenyon & Kenyon LLP

(57) ABSTRACT

A method for determining a variable which represents the condition of a driver of a vehicle, the variable being determined independently of the time using at least one other variable representing the light intensity to which the driver is exposed.

21 Claims, 2 Drawing Sheets

(56) References Cited

U.S. PATENT DOCUMENTS

| | | |
|---|---|---|
| 6,313,749 B1 | 11/2001 | Horne et al. |
| 8,918,227 B2* | 12/2014 | Junge et al. ............... 700/306 |
| 2005/0163383 A1* | 7/2005 | Kim ................. G06K 9/00597 382/209 |
| 2006/0202843 A1* | 9/2006 | Ota ................... G06K 9/2036 340/576 |
| 2008/0120025 A1* | 5/2008 | Naitou et al. ............... 701/207 |
| 2010/0079294 A1 | 4/2010 | Rai et al. |
| 2013/0015010 A1* | 1/2013 | Junge et al. ............... 180/272 |
| 2013/0076885 A1* | 3/2013 | Kobetski ............... A61B 5/18 348/78 |
| 2014/0139655 A1* | 5/2014 | Mimar ............. G08B 21/0476 348/77 |
| 2014/0221781 A1* | 8/2014 | Schrauf ............... A61B 5/0205 600/301 |
| 2014/0276090 A1* | 9/2014 | Breed ................... A61B 5/18 600/473 |

FOREIGN PATENT DOCUMENTS

| | | |
|---|---|---|
| DE | 43 38 244 | 5/1994 |
| DE | 100 39 795 | 3/2002 |
| DE | 103 59 125 | 7/2005 |
| DE | 10 2005 055971 | 5/2007 |
| DE | 10 2009 016936 | 11/2009 |
| DE | 10 2009 009975 | 4/2010 |
| JP | 2005006966 A | 1/2005 |
| WO | 2008120312 A1 | 10/2008 |

* cited by examiner

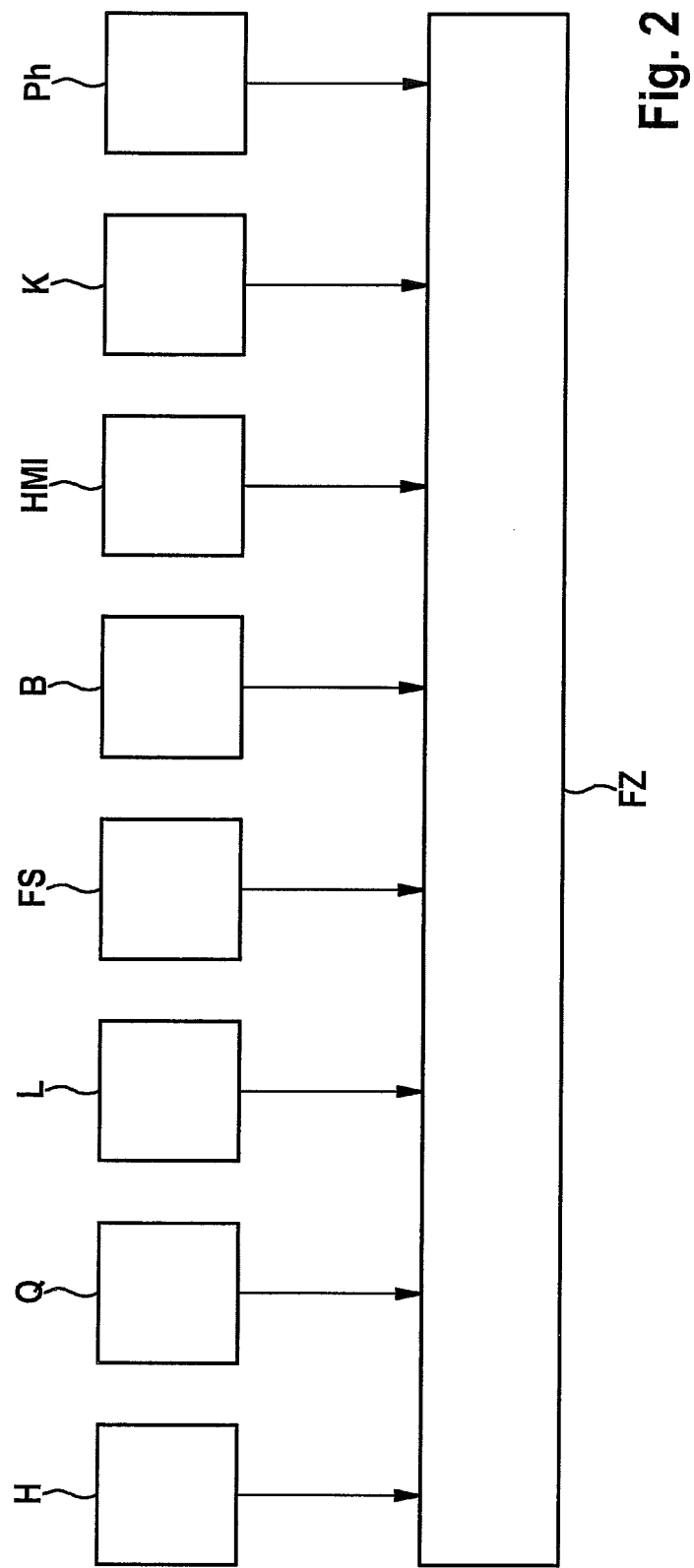

METHOD AND DEVICE FOR DETECTING THE CONDITION OF A DRIVER

FIELD OF THE INVENTION

The field of the invention is a method and device for detecting the condition of a driver.

BACKGROUND INFORMATION

Methods for determining the fatigue of a machine operator based on an evaluation of the circadian rhythm are known from U.S. Pat. No. 6,313,749 E1. The circadian rhythm is determined using time values as input variables.

SUMMARY OF THE INVENTION

The present invention is directed to a method for determining a variable representing the condition of the driver of a vehicle, which is determined from another variable representing the light intensity to which the driver is exposed.

This method is carried out independently of the time. For this purpose, the light intensity is determined with the aid of a sensor and, based on the light intensity thus measured, the condition of a driver is determined.

From medical studies, it is known that light intensity acting on a human has a notable influence on his/her condition such as, for example, fatigue and/or the ability to respond.

The time-independent determination according to the present invention of the variable representing the condition of a driver based on light intensity results in the advantage that errors are avoided which, in the case of time value-based evaluations, may be caused by false time values.

Another advantage results by avoiding effects which are associated with the geographic position of the vehicle, and which occur when, for example, the determination of the condition of the driver is based on Central European correlations between light intensity values and time values.

For example, seasonally dependent time durations of varying length exist between sunrise and sunset, as a function of the geographic latitude. In parts of Scandinavia, for example, this means on the one hand that in December it is completely dark in the early afternoon (around 4:00 p.m.), while on the other hand on the summer solstice it is still light even at night (around midnight).

In addition, when traveling through regions for which the same time zone is established across multiple degrees of longitude (for example, the People's Republic of China), discrepancies may also occur between the actual condition of a driver resulting from light intensity and the condition of a driver ascertained on the basis of a time value.

In both cases, a determination of the condition of a driver based solely on time values and taking into consideration correlations between Central European time value and light intensity value may not be optimal, since they do not account for the fact that the driver finds him/herself exposed to a light intensity or darkness which is atypical or unusual for the time value.

According to one advantageous embodiment of the present invention, the variable representing the condition of a driver may be determined directly from another variable representing the light intensity to which the driver is exposed. According to this embodiment, additional variables may also be considered in the determination of the condition of a driver. According to this embodiment, the condition of a driver is determined taking multiple independent components into consideration, whereby the variable representing light intensity may be used for directly determining an independent component.

In another advantageous embodiment of the method, a time filter (for example, a dead time element) is used in determining the light intensity. The use of a time filter results according to the present invention in the advantage that conditions road-structural (for example, tunnels or avenues) or meteorological (for example, brief thunderstorms) in nature, which result in brief and short-lived intervals of reduced light intensity, may be considered. The use of a time filter ensures that short-term changes in light intensity may be weighted less heavily than longer term changes. For this purpose, it is conceivable for a time threshold value to be used, and only after a longer lasting change in light intensity is the condition of a driver also considered to be changed.

The variable representing the condition of the driver may be fatigue.

The reason for determining fatigue is the fact that, in particular, the development of fatigue in humans is influenced significantly by the light intensity humans are able to perceive.

The light intensity in the form of illuminance may be measured in lux. Measuring the illuminance in lux ensures that comparable and physically precisely defined measured values may be used as a basis for calculating the condition, in particular, the fatigue, of a driver.

To determine light intensity, in particular illuminance, light sensors may be used.

In addition to the variable representing the condition of a driver, other variables also representing the condition of a driver may advantageously also be used. By considering these additional variables, it is possible to weight and corroborate the variable according to the present invention, which is independent of the time and based on an evaluation of light intensity.

The specific embodiments for determining additional variables representing the condition of a driver are described below.

Advantageously, the lateral guidance behavior, in particular the steering behavior of the driver, is incorporated in the determination of the variable representing the condition of a driver. Also incorporated in the determination of the variable representing the condition of a driver may be the longitudinal guidance behavior, in particular the actuation of the pedals by the driver.

In another embodiment, the ability of the driver to maintain the vehicle within one traffic lane is taken into consideration when determining the variable representing the condition of a driver.

The evaluation of the driving behavior forms part of the related art and represents a very good opportunity for assessing the condition of a driver.

Advantageously, the activation of the operational controls, for example, the blinker and/or the power windows by the driver, is also incorporated in the determination of the variable representing the condition of a driver.

The interaction of the driver with the vehicle via HMI and infotainment systems, such as an integrated navigation system and/or a voice control and/or a voice output, may be incorporated in the determination of the variable representing the condition of a driver.

Determination of the condition of a driver while taking into consideration the analysis of the interaction of the driver with HMI (human-machine interface) and infotainment systems also has the advantage of actively determining the condition of a driver, for example, using reaction times.

In another advantageous embodiment of the present invention, an additional variable, which is ascertained via a vehicle interior camera for driver monitoring, is also taken into consideration in determining the variable representing the condition of a driver.

Finally, another variable, which represents at least one physiological condition of the driver, may be taken into consideration in determining the variable representing the condition of the driver.

The variable representing a physiological driver condition which is taken into consideration in determining the variable(s) representing the condition of a driver is/may be the body temperature and/or the heart rate of the driver.

Advantageously, sensors are used for determining the physiological variables, which are mounted in the rear view mirror and/or in the driver's seat and/or in the driver's seat belt and/or in the steering wheel.

In particular, the data relating to the physiological driver condition (illness, stress) ascertained with the aid of the aforementioned sensors are suited for more precisely determining the condition of a driver and to corroborate the condition of a driver determined according to the present invention.

To determine a variable representing the condition of a driver of a vehicle, a device may be used with which the variable representing the light intensity to which the driver is exposed is determined at least based on one other variable independently of the time.

Additional embodiments of the present invention are reflected in the subclaims.

The present invention is explained in the following paragraph with reference to exemplary embodiments, from which additional inventive features may arise, but to which the scope of the present invention is not limited. The embodiments are represented in the drawings.

BRIEF DESCRIPTION OF THE DRAWINGS

FIG. 2 schematically shows a representation of the determination of the condition of a driver based on multiple independent components.

DETAILED DESCRIPTION

Figure 1:
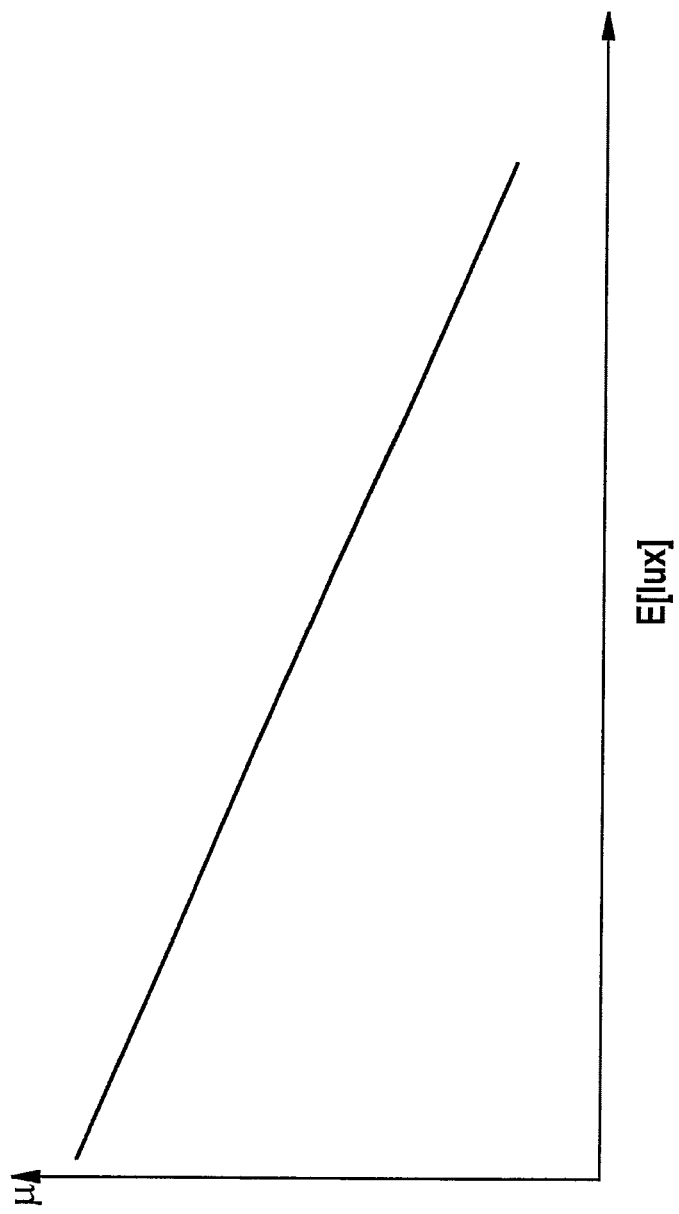
FIG. 1 schematically shows a representation of the connection between fatigue and light intensity.

FIG. 1 schematically shows the connection between fatigue ($\mu$) and light intensity (E). Fatigue ($\mu$) is plotted on the y-axis in relation to light intensity (E) in lux on the x-axis. This shows that fatigue ($\mu$) decreases with increasing light intensity (E). The connection in this case is linear and may be used for a direct determination of fatigue ($\mu$) as a result of light intensity (E).

In addition to fatigue ($\mu$), other variables representing the condition (FZ) of a driver may be plotted on the y-axis in relation to light intensity (E) on the x-axis. The variables representing the condition of a driver would be plotted as changeable variables as a function of light intensity (E).

FIG. 2 depicts the determination of the condition of a driver (FZ) based on multiple independent components. The condition of a driver is determined primarily by taking into consideration a variable (H) representing the light intensity. Other variables apart from light intensity may also be considered and used for determining the condition of a driver.

The other variables which may be considered when determining the condition (FZ) of a driver may be ascertained based on: lateral guidance behavior (Q), in particular, the steering angle behavior, the longitudinal guidance behavior (L), in particular the actuation of the pedals, the traffic lane behavior (FS), the actuation of the operational controls (B), for example, blinkers and/or power windows, the interaction with HMI systems (HMI), data ascertained using the vehicle interior camera (K), and the physiological condition of the driver (Ph).

The list of reference numerals is as follows:
$\mu$ fatigue
E light intensity
H a variable representing the light intensity (E)
Q lateral guidance behavior
L longitudinal guidance behavior
FS traffic lane behavior
B actuation of operational controls
HMI human-machine interface
K data ascertained using the vehicle interior camera
Ph physiological condition
FZ condition of a driver

What is claimed is:

1. A method for determining a variable representing a condition of a driver of a vehicle, the method comprising:
    determining, via a processor, the variable independently of a time using at least one other variable, which represents a light intensity to which the driver is exposed;
    wherein the variable, which represents the light intensity to which the driver is exposed, is use-able to directly determine the variable representing the condition of a driver.

2. The method of claim 1, wherein the variable, is determinable using a time filter which includes a dead time element.

3. The method of claim 1, wherein the variable representing the condition of a driver is driver fatigue.

4. The method of claim 1, wherein the light intensity is measured in the form of illuminance.

5. The method of claim 1, wherein light sensors are used to determine light intensity.

6. The method of claim 1, wherein the lateral guidance behavior is incorporated in the determination of the variable representing the condition of a driver.

7. The method of claim 1, wherein the longitudinal guidance behavior is incorporated in the determination of the variable representing the condition of a driver.

8. The method of claim 1, wherein the ability of the driver to maintain the vehicle preferably within one traffic lane is incorporated in the determination of the variable representing the condition of a driver.

9. The method of claim 1, wherein the actuation of operating controls is incorporated in the determination of the variable representing the condition of a driver.

10. The method of claim 1, wherein the interaction of the driver with the vehicle via HMI systems and infotainment systems is incorporated in the determination of the variable representing the condition of a driver.

11. The method of claim 1, wherein another variable, which is ascertained via a vehicle interior camera for driver monitoring, is incorporated in the determination of the variable representing the condition of a driver.

12. The method of claim 1, wherein another variable, which represents at least one physiological condition of the driver, is incorporated in the determination of the variable representing the condition of a driver.

13. The method of claim 12, wherein the physiological variables of the driver includes at least one of a body temperature and a heart rate.

14. The method of claim 12, wherein sensors are used for determining the physiological variables, these sensors being mounted in at least one of a rear view mirror, a the driver's seat, a driver's seat belt and a steering wheel.

15. The method of claim 1, wherein the lateral guidance behavior, which includes the steering behavior of the driver, is incorporated in the determination of the variable representing the condition of a driver.

16. The method of claim 1, wherein the longitudinal guidance behavior, which includes the actuation of the pedals by the driver, is incorporated in the determination of the variable representing the condition of a driver.

17. The method of claim 1, wherein actuation of operating controls, including a blinker and/or power windows, by the driver is incorporated in the determination of the variable representing the condition of a driver.

18. The method of claim 1, wherein the interaction of the driver with the vehicle via HMI systems and infotainment systems, including at least one of an integrated navigation system, a voice control and a voice output, is incorporated in the determination of the variable representing the condition of a driver.

19. The method of claim 1, wherein the condition of the driver is the sleepiness of the driver.

20. A device for determining a variable representing a condition of a driver of a vehicle, comprising:
 a determining arrangement to determine, via a processor, the variable independently of a time, using at least one other variable, which represents a light intensity to which the driver is exposed;
 wherein the variable, which represents the light intensity to which the driver is exposed, is use-able to directly determine the variable representing the condition of a driver.

21. The device of claim 20, wherein the condition of the driver is the sleepiness of the driver.

* * * * *